United States Patent [19]
Wiegert

[11] 4,125,599
[45] Nov. 14, 1978

[54] X-RAY CONTRAST AGENTS

[75] Inventor: Philip E. Wiegert, Glens Falls, N.Y.

[73] Assignee: Mallinckrodt, Inc., St. Louis, Mo.

[21] Appl. No.: 715,974

[22] Filed: Aug. 19, 1976

[51] Int. Cl.$^2$ .................... C07C 103/24; A61K 29/02
[52] U.S. Cl. ................................ 424/5; 260/501.11;
260/501.16; 562/451; 562/437; 562/455;
560/264; 560/251
[58] Field of Search ...................... 260/501.11, 501.16,
260/518 A, 519; 424/5

[56] References Cited
U.S. PATENT DOCUMENTS

| | | | |
|---|---|---|---|
| 3,145,197 | 8/1964 | Hoey .............................. | 260/515 A |
| 3,622,616 | 11/1971 | Guerbet .......................... | 260/501.11 |
| 3,701,771 | 10/1972 | Almen et al. .................... | 536/55 |
| 3,702,866 | 11/1972 | Salvesen et al. ................ | 260/501.11 |
| 4,021,481 | 5/1977 | Almen et al. .................... | 424/5 |

Primary Examiner—James O. Thomas, Jr.
Assistant Examiner—G. T. Breitenstein
Attorney, Agent, or Firm—Koenig, Senniger, Powers and Leavitt

[57] ABSTRACT

5-Gluconamido-2,4,6-triiodo-N-methylisophthalamic acid, 3-acetamido-2,4,6-triiodo-5-trishydroxymethylacetamidobenzoic acid, related compounds and salts and esters thereof are useful as x-ray contrast agents. The corresponding acyl halides are useful as intermediates.

7 Claims, No Drawings

X-RAY CONTRAST AGENTS

BACKGROUND OF THE INVENTION

This invention relates to the field of organic chemistry and more particularly to 5-gluconamido-2,4,6-triiodo-N-methylisophthalamic acid, 3-acetamido-2,4,6-tiiodo-5-trishydroxymethylacetamido-benzoic acid, related compounds and certain salts, esters and acyl halides thereof. The acids, salts and esters are useful as x-ray contrast agents.

Many 2,4,6-triiodobenzoic acid derivatives have been proposed for use as x-ray contrast agents. These include, as a subgroup, many 2,4,6-triiodoisophthalamic acid derivatives such as 5-acetamido-2,4,6-triiodo-N-methylisophthalamic acid and its salts (G. B. Hoey, U.S. Pat. No. 3,145,197 (1964). The coined terms "iothalamic acid" and "iothalamate" have been applied to these compounds. A profuse literature relating to the radiological uses of these compounds have been published in succeeding years.

Certain N-hydroxyalkyl-2,4,6-triiodoisophthalamic acids have also been disclosed. For example, Guerbet U.S. Pat. No. 3,622,616 and Salvesen et al. U.S. Pat. No. 3,702,866 disclose 5-acetamido-N-(2-hydroxyethyl)-2,4,6-triiodoisophthalamic acid. In addition, Salvesen et al. also disclose the compound N-(3-acetamido-5-carboxy-2,4,6-triiodobenzoyl)-N-methylglucamine which may also be designated 5-acetamido-N-(D-gluco-1-deoxy-2,3,4,5,6-pentahydroxyhexyl)-2,4,6-triiodo-N-methylisophthalamic acid.

Further, Almen et al. (U.S. Pat. No. 3,701,771) disclose a considerable number of non-ionic N-(2,4,6-triiodobenzoyl)-amines said to be useful as x-ray contrast agents in the cerebrospinal cavities, including one (compound 41) derived from tris (hydroxymethyl) aminomethane. This compound is designated as N-[3-N-methylacetamido-5-N-(beta-hydroxyethyl)-acetamido-2,4,6-triiodobenzoyl] N-[tris(hydroxymethyl)-methyl] amine. This compound was reported to have a rather low water solubility (0.86%) although many other compounds in the series were disclosed to be relatively highly soluble in water.

The use, as x-ray contrast media, of aqueous solutions of salts of various 2,4,6-triiodoisophthalamic and other 2,4,6-triiodobenzoic acids with pharmaceutically acceptable cations such as sodium, calcium and magnesium and alkanolamines such as ethanolamine, diethanolamine and meglumine (N-methylglucamine) is well known to those skilled in the art.

SUMMARY OF THE INVENTION

Among the objects of the invention may be mentioned the provision of new isophthalamic acid derivatives; the provision of new 2,4,6-triiodoisophthalamic acid compounds; the provision of compounds of the type indicated which are useful for the preparation of roentgenographic contrast media; and the provision of methods of preparing such compounds. Other objects and features will be in part apparent and in part pointed out hereinafter.

The present invention is thus directed to the compounds of the formula:

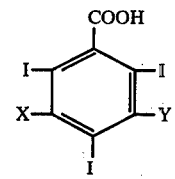

wherein X is selected from the group consisting of lower acylamino, N-(lower alkyl)-lower acylamino, N-(hydroxy lower alkyl)-lower acylamino, carbamyl, N-(lower alkyl) carbamyl and ureido and Y is selected from the group consisting of gluconamido and trishydroxymethylacetamido, and salts and acyl halides and esters thereof. More particularly, the invention is directed to 5-gluconamido-2,4,6-triiodo-N-methylisophthalamic acid, 3-acetamido-2,4,6-triiodo-5-trishydroxymethylacetamido-benzoic acid and salts and acyl halides and ester derivatives thereof. The invention is also directed to a method of preparing a compound of the formula:

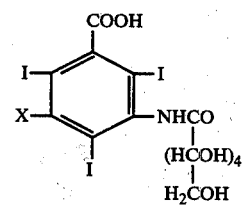

wherein X is selected from the group consisting of lower acylamino, N-(lower alkyl)-lower acylamino, N-(hydroxy lower alkyl)-lower acylamino, carbamyl, N-(lower alkyl) carbamyl and ureido which comprises the steps of acylating a compound of the formula:

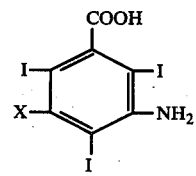

wherein X is as defined above, by reacting it with penta-O-acetylgluconyl chloride and hydrolyzing the resultant compound. The invention is further directed to the method of preparing 3-acetamido-2,4,6-triiodo-5-trishydroxymethylacetamido-benzoic acid which comprises reducing 3-nitro-trishydroxymethylacetamido-benzoic acid, iodinating the 3-amino-5-trishydroxymethylacetamido-benzoic acid to form 3-amino-2,4,6-triiodo-5-trishydroxymethylacetamido-benzoic acid, and acylating the 3-amino-2,4,6-triiodo-5-trishydroxymethylacetamido-benzoic acid to form 3-acetamido-2,4,6-triiodo-5-trishydroxymethylacetamido-benzoic acid.

DESCRIPTION OF THE PREFERRED EMBODIMENTS

In accordance with the present invention, it has now been found that compounds of the following formula:

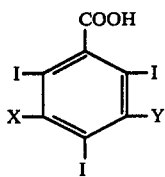

wherein X is selected from the group consisting of lower acylamino, N-(lower alkyl)-lower acylamino, N-(hydroxy lower alkyl)-lower acylamino, carbamyl, N-(lower alkylcarbamyl and ureido and Y is selected from the group consisting of gluconamido and trishydroxymethylacetamido, and salts and acyl halides and esters thereof are useful as x-ray contrast agents. The salts of these acids with pharmaceutically acceptable cations are useful in the preparation of x-ray contrast media intended primarily for intravascular administration. Other salts, such as ammonium salts, are useful as intermediates. Esters of the acids of the invention are useful in x-ray contrast media intended primarily for use in instillation procedures. Acyl halide derivatives of the acids are useful as intermediates for the preparation of amides and other non-ionic derivatives.

The substituents which may constitute X in the above formula include the following: lower acylamino, e.g., acetamido and propionamido; N-(lower alkyl)-lower acylamino, e.g., N-methylacetamido and N-methylpropionamido; N-(hydroxy lower alkyl)-lower acylamino, e.g., N-(hydroxy ethyl)-acetamido and N-(hydroxy ethyl)-propionamido; carbamyl; N-(lower alkyl) carbamyl, e.g., N-methylcarbamyl and N-ethylcarbamyl; and ureido. As used herein, the term "lower" (e.g., lower alkyl and lower acylamino) means that the function contains between 1 and 6 carbon atoms.

In the preparation of 5-gluconamido-2,4,6-triiodo-N-methylisophthalamic acid and related compounds of the formula:

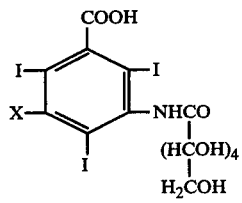

wherein X is selected from the group consisting of lower acylamino, N-(lower alkyl)-lower acylamino, N-(hydroxy lower alkyl)-lower acylamino, carbamyl, N-(lower alkyl) carbamyl and ureido, a compound of the following formula is first acylated with penta-O-acetylgluconyl chloride:

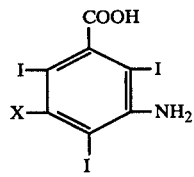

wherein X is as defined above; and the resultant compound is then hydrolyzed. The acylation reaction is carried out utilizing a polar aprotic solvent, preferably N,N-dimethylacetamide, as a reaction medium. Other polar aprotic solvents that may be utilized include dimethylformamide, N-methylpyrrolidone, etc.

In the preparation of the 3-acetamido-2,4,6-triiodo-5-trishydroxymethylacetamido-benzoic acid of the invention, 3-nitro-trishydroxymethylacetamido-benzoic acid is reduced to form 3-amino-5-trishydroxymethylacetamido-benzoic acid. The latter is then iodinated to form 3-amino-2,4,6-triiodo-5-trishydroxymethylacetamido-benzoic acid, after which the 3-amino compound is acylated to form the desired 3-acetamido-2,4,6-triiodo-5-trishydroxymethylacetamido-benzoic acid.

5-Gluconamido-2,4,6-triiodo-N-methylisophthalamoyl chloride, 3-acetamido-2,4,6-triiodo-5-trishydroxymethylacetamidobenzoyl chloride or other acyl halides of the invention may be made by the following general method.

The acids of the invention may be treated with excess thionyl halide in N,N-dimethylacetamide. After removing the unreacted thionyl halide by evaporation under reduced pressure, the product is suitable for use as an intermediate in situ. Alternatively, the product is isolated by evaporating the solvent under vacuum.

The lower alkyl 5-gluconamido-2,4,6-triiodo-N-methylisophthalamates and 3-acetamido-2,4,6-triiodo-5-trishydroxymethylacetamidobenzoates of the invention may be prepared by the following general method. Either a 5-gluconamido-2,4,6-triiodo-N-methylisophthalamoyl halide or a 3-acetamido-2,4,6-triiodo-5-trishydroxymethylacetamidobenzoyl halide with the hydroxyl groups in a suitable protected form is treated with excess anhydrous lower alkanol in, for example, N,N-dimethylacetamide, in the presence of potassium carbonate. After reaction is complete, the protecting groups are removed in a suitable manner, the reaction mixture is filtered to remove the inorganic salts and the lower alkyl 5-gluconamido-2,4,6-triiodo-N-methylisophthalamate or 3-acetamido-2,4,6-triiodo-5-trishydroxymethylacetamidobenzoate is isolated by evaporating the excess alcohol and the solvent.

EXAMPLE 1

Preparation of
5-Gluconamido-2,4,6-triiodo-N-methylisophthalamic Acid

1. Preparation of 5-Penta-O-acetyl-D-gluconamido-2,4,6-triiodo-N-methylisophthalamic Acid; II

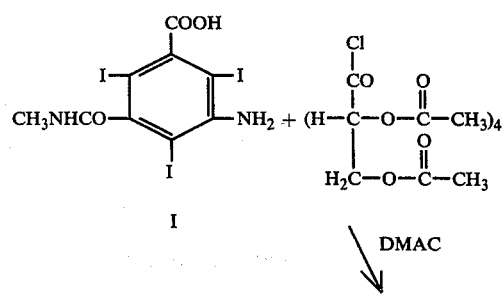

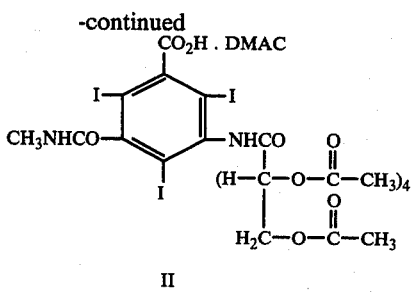

II

Dried 5-amino-2,4,6-triiodo-N-methylisophthalamic acid (I; 0.5 mole, 286 g.) was added in one portion to N,N-dimethylacetamide (DMAC, 858 ml.) in a 3-liter three-necked flask equipped with a stirrer, thermometer, drying tube (CaCl$_2$) and condenser. The 5-amino-2,4,6-triiodo-N-methylisophthalamic acid mostly dissolved and the temperature was held to 25°–30° C. with a water bath. Five minutes later penta-O-acetyl-gluconyl chloride (318 g., 0.75 mole) was added in one portion. Stirring was continued for 140–164 hours at 26° C. A clear solution was obtained after 1–2 days of stirring. The reaction was followed by thinlayer chromatography. Aliquots were taken periodically, the N,N-dimethylacetamide was removed from the aliquots on a rotovapor under reduced vacuum and the residue was examined in two thin-layer chromatographic systems (benzenemethyl ethyl ketone-formic acid (97%), 60:25:25; and isobutanol-isopropanol-ammonium hydroxide, 100:40:50). When it was concluded that the reaction was complete (140 hrs.), the N,N-dimethylacetamide was removed on the rotovapor at 50°–82° (1–10 mm). Yield of II: 801.44 g. of brown gum.

2. Preparation of 5-Gluconamido-2,4,6-triiodo-N-methylisophthalamic Acid; III

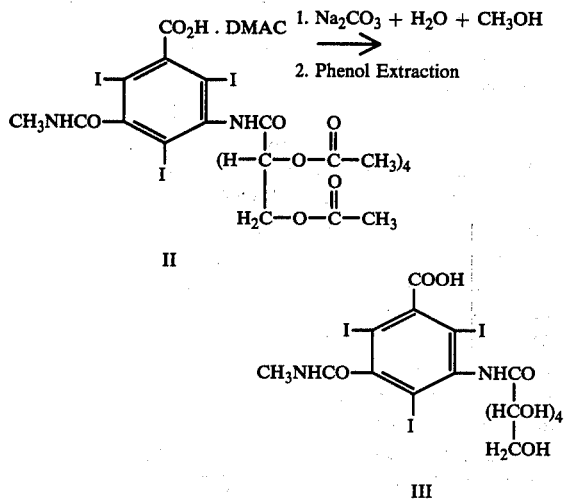

(a) Hydrolysis

The 5-penta-O-acetyl-D-gluconamido-2,4,6-triiodo-N-methylisophthalamic acid (II; 801.4 g.) without further purification was dissolved in a 50:50 methanol-water mixture (42 l.) and sodium carbonate (278 g., 5.25 equivalent) was added. The hydrolysis was followed by thin-layer chromatography using a benzene-methyl ethyl ketone-formic acid (60:25:25) system. The reaction was quenched after 2½ hours of hydrolysis by adding 12% w/v hydrochloric acid to a pH of 4–5.

(b) Phenol extraction

The hydrolysis solution (43 l.) was concentrated on rotovators at 55°–60° C. under aspirator and house vacuums to 2500 ml. The 2500 ml. of reaction mixture was acidified to pH 1.0 with concentrated hydrochloric acid (175 ml.) and extracted with 90% aqueous phenol (45 ml. H$_2$O/lb. of phenol). Five 350 ml. phenol extractions were used. All extractions were done with a mechanical stirrer in a beaker and the layers were separated in a separatory funnel. The combined phenol extracts were washed with 2 × 250 ml. of water and 5 × 350 ml. of water. Ether (5250 ml.) was added to the phenol extracts, and the oil that precipitated was extracted into water (5 × 700 ml.). The water extracts were back washed with ether (4 × 500 ml.). A thin-layer chromatogram (benzene-methyl ethyl ketone-formic acid, 60:25:25) taken at this time showed that there was product left (a) in the mother liquor and (b) in the water wash of the combined phenol extracts. The product left behind in these two liquors was actually purer than the product in the main extract. These liquors were concentrated and reextracted (see (c) below).

The main water extract was concentrated to an oil on a rotovapor (55°–60° C./1–10 mm), yield 261.0 g., and crystallized from boiling isopropyl alcohol (1500 ml.), yield 155.83 g. (the sample was submitted for nuclear magnetic resonance examination; isopropyl alcohol was present). A thin-layer chromatographic examination of the 155.8 g. product (benzene-methyl ethyl ketone-formic acid (97%), 60:25:25; and isobutanol-isopropanol-ammonium hydroxide, 100:40:50) showed very little 5-amino-2,4,6-triiodo-N-methylisophthalamic acid left as an impurity but some of the unknown that runs at the same place as the pentaacetate starting material. No further work was done with this portion of product.

(c) Phenol Extractions of Mother Liquor and Wash

The mother liquor from the above extraction (3500 ml.) was concentrated on the rotovapor to 800 ml. (aspirator, 60°–65° C.) and extracted with 4 × 160 ml. of 90% phenol. The phenol extracts were washed with 4 × 70 ml. of water, then ether (2400 ml.) was added and the ether-phenol was extracted with 4 × 200 ml. of water. The combined water extractions were back extracted with 3 × 200 ml. of ether and the water was concentrated to dryness on the rotovapor under aspirator vacuum at 55°–60° C. and finally at 60° C./0.2 mm for 45 minutes; yield 15.73 g.

The water wash from the main extract ((b) above, 2500 ml.) was concentrated on the rotovapor to 300 ml., and extracted with 3 × 60 ml. of 90% phenol at pH 1. The phenol layer (about 400 ml.) was washed with 4 × 80 ml. of water, ether (1125 ml.) was added to the phenol layer and the ether-phenol solution was extracted with 4 × 100 ml. of water. The water layer was back washed with 3 × 80 ml. of ether and evaporated on the rotovapor under aspirator vacuum at 55°–60° C. and finally at 60° C./0.2 mm for 45 minutes; yield 84.53 g. The thin-layer chromatogram (benzene-methyl ethyl ketone-formic acid, 60:25:25 and isobutanol-isopropanol-ammonium hydroxide, 100:40:50) of this fraction and the 15.23 g. fraction were similar. There was mainly a product spot with a small amount of 5-amino-2,4,6-triiodo-N-methylisophthalamic acid and traces of two unknowns. The two fractions were combined (100.26 g.) and slurried in boiling isopropyl alcohol (3500 ml.) for one hour. The slurry (2500 ml. volume) was stirred without cooling and with intermittent scratching. At 40° C. the first crop was collected, yield 40.05 g. (air dried 40 hours, then 2–3 hours at 60°–65° C.

in vacuum oven). A second crop was collected after the mother liquor had air evaporated to 1250 ml.; yield 11.20 g. (dried at 60°–65° C. 2–3 hours in a vacuum oven). A third crop of 15 g. was collected but not used nor was the mother liquor. The thin-layer chromatograms taken of the first and second crops were similar (in the previously described formic acid and ammoniacal systems). The thin-layer chromatograms showed a single product with a small amount of 5-amino-2,4,6-triiodo-N-methylisophthalamic acid as an impurity plus a trace of an unknown. The two crops were combined and submitted for nuclear magnetic resonance examination. Isopropyl alcohol was trapped in the product, so the sample was dissolved in water (350 ml.), filtered to remove a haze, and evaporated on the rotovapor at 50° C./0.2 mm.

A sample of this material was dried at 56° C. in an Abderhalden drying pistol at 0.1–0.2 mm for 18 hours. The water content by loss-on-drying was 4.84% plus an additional 0.92% of water as shown by Karl Fisher titration. This material was used for a neutral equivalent, found/theory, 754.0/750.0 and sent for elemental analysis.

Calculated for $C_{15}H_{17}I_3N_2O_9$: C, 24.02%; H, 2.28%; I, 50.76%; N, 3.74%. Found: C, 23.57%; H, 2.52%; I, 48.79%; N, 3.87%. Examination by thin-layer chromatography in two systems (benzene-methyl ethyl ketone-formic acid, 60:25:25 and isobutanol-isopropanol-ammonium hydroxide, 100:40:50) showed a single spot with some 5-amino-2,4,6-triiodo-N-methylisophthalamic acid plus a small amount of another impurity. Infrared and nuclear magnetic resonance spectra are in agreement with the postulated structure.

EXAMPLE 2

Preparation of Sodium 5-Gluconamido-2,4,6-triiodo-N-methylisophthalamate

5-Gluconamido-2,4,6-triiodo-N-methylisophthalamic acid (9.28 g.) was stirred with water (ca. 5 ml.) and 50% sodium hydroxide solution was added to achieve a pH of 7.17. The resulting solution was concentrated under reduced pressure (25° C., 1 mm.) to provide sodium 5-gluconamido-2,4,6-triiodo-N-methylisophthalamate.

The solubility of the sodium salt was greater than 101%. After standing for over five months at 5°–10° C. no crystals formed.

EXAMPLE 3

Preparation of 3-Acetamido-2,4,6-triiodo-5-(trishydroxymethyl)acetamido-benzoic Acid 1. Preparation of trisacetoxymethyl-acetic Acid; II

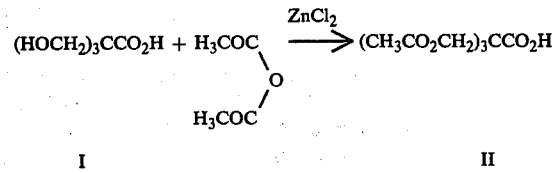

Granular zinc chloride (9 g.) was added to acetic anhydride (450 ml.). The slurry was stirred 45 minutes to dissolve most of the zinc chloride. Trimethylol acetic acid (I; 89.87 g. (0.6 mol) was added in one portion. The temperature rose in 2–3 minutes to 85° C. and was cooled with an ice bath to prevent a higher temperature rise. All the solids dissolved and the solution was stirred 1½ hours at 45°–70° C. When the solution cooled to 45° C., it was poured into water (900 ml.) at 25° C. The water was extracted with ether (4 l.), the ether was dried overnight with sodium sulfate and concentrated under aspirator vacuum at 47° C. on a rotovapor and with a vacuum pump at 50°–62° C./1 mm. The solid residue, 173.81 g., was recrystallized from carbon tetrachloride (550 ml.), collected and dried 4 hours at 70° C. M.P. 88°–91.5° C., yield 155.69 g., 94%; N.E. found/theory, 277.8/276.3 (reported M.P. 85°–90° C., K. Hayns, Ber., 89, 1648 (1956)).

2. Preparation of Trisacetoxymethylacetyl Chloride; III

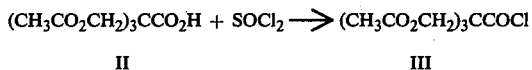

Thionyl chloride (434 ml.) was placed in a 3-liter, 3-necked flask fitted with stirrer, heating mantle and a calcium chloride drying tube. Trisacetoxymethyl acetic acid (II; 155 g., 0.55 mole) was added in one portion. The solid dissolved readily and the solution was refluxed at 74–78° C. for one-half hr. Excess thionyl chloride was removed with an aspirator at 55° C. (bath temp.).

Some of the residue that remained after removal of excess thionyl chloride was charred from overheating. Benzene (650 ml.) was added to the solidified residue and the solution was decanted from the tar. A total of 1150 ml. of benzene was distilled from the decanted solution at 37–75° C. (bath temperature) under aspirator vacuum. Distillation was stopped when the pot temperature reached 75° C. The residue was extracted with petroleum ether (750 ml.) for 15 minutes and again with petroleum ether (1400 ml.) for 1.5 hours. The petroleum ether was decanted and the solid was placed in the dessicator under house vacuum overnight, M.P. 74–77° C.; yield 133.62 g., 82.4% (reported 61%, M.P. 78° C., K. Hayns, Ber. 89, 1648 (1956).

3. Purification of 3-Amino-5-nitrobenzoic Acid.

3-Amino-5-nitrobenzoic acid containing about 20–30% dinitrobenzoic acid was slurried in water (1820 ml.), concentrated hydrochloric acid (182 ml.) was added and the slurry was stirred and warmed to dissolve everything. After cooling to 25–30° C. the solution was extracted three times with 1 liter of $CH_2Cl_2$ using magnetic stirring. Sodium hydroxide (50%) was added to the aqueous layer to pH 3, and the yellow solid that precipitated was collected and dried at 75–80° C. overnight at 105° C. (3 hours), yield 70.5 g. Most of the dinitrobenzoic acid was removed leaving about 1–2%.

4. Preparation of 3-Nitro-5-trisacetoxymethylacetamido-benzoic Acid; IV

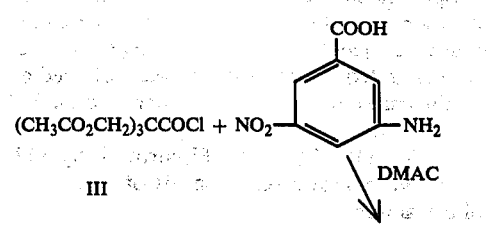

-continued

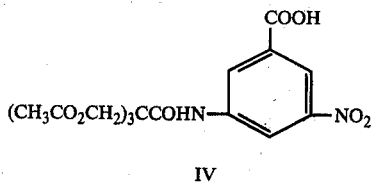

Dry 3-amino-5-nitrobenzoic acid (56.75 g., 0.311 mol) was dissolved in N,N-dimethylacetamide (DMAC, 568 ml.). Trisacetoxymethylacetyl chloride (III; 113.42 g., 0.385 mol) was added in one portion. The temperature rose to 45° C. (no cooling) and the solution was stirred at room temperature over the weekend. The reaction appeared complete by thin-layer chromatography (benzene-methyl ethyl ketone-acetic acid, 90:25:5) and the DMAC was removed on the rotovapor at 82° C./0.5 mm. The gummy residue, 249.4 g., was triturated with water (1092 ml.) and, after standing one-half hour, solidified. The solid was pulverized, reslurried in water, and collected to yield 161 g. of a wet solid (theory 136.8 g.).

5. Preparation of 3-Nitro-trishydroxymethylacetamido-benzoic Acid; V

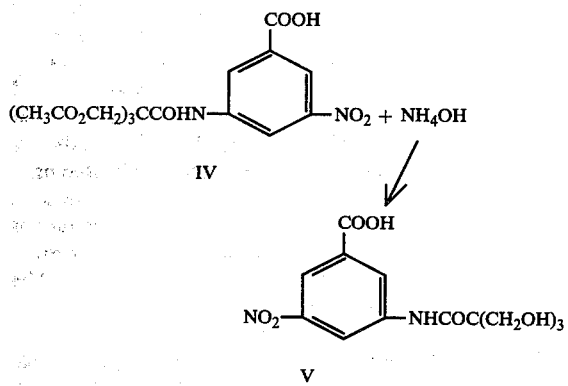

The wet solid (IV; 161 g.) from the previous step 4 was slurried in water (1240 ml.), concentrated ammonium hydroxide (390 ml.) was added, and the solution was stirred at 60° C. for 2 hours.

The water was removed on the rotovapor at 50° C. with aspirator vacuum leaving a yellow solid. The yellow solid was dissolved in water (468 ml.) and acidified with concentrated hydrochloric acid (109 ml.) at 25–30° C. After stirring 1 hour at 25° C. and 1 hour at 0°–5° C. the solid was collected to yield 89.6 g. (91.7%). This material was recrystallized from hot water (4 ml. of water per gram) and treated with charcoal (5 g.) for 10 minutes at 90° C. A yellow solid crystallized and was collected to yield 94.6 g. The overall yield after acylation and hydrolysis was 85.8%.

The N.E. was found/theory 317.9/314.2. Two small impurities could be seen by thin-layer chromatography (isobutyl alcohol-isopropyl alcohol-ammonium hydroxide, 100:40:30).

6. Preparation of 3-Amino-2,4,6-triiodo-5-trishydroxymethylacetamido-benzoic Acid; VI

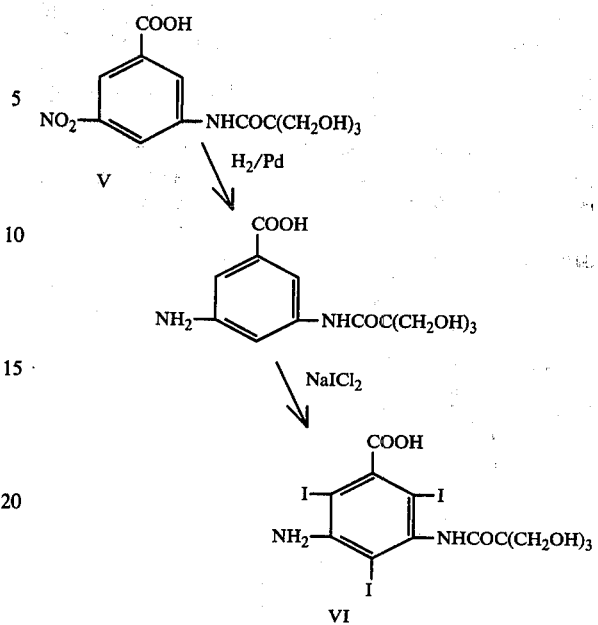

(a) Reduction

A solution of the nitro compound (V; 58.27 g., 0.185 mol) dissolved in water with 20% sodium hydroxide (186 ml.) at pH 6.3. The solution was treated with charcoal (2 g.) and 5% Pd/C (1 g.) for 15 minutes, filtered and transferred to a liter Parr shaker bottle (volume 270–300 ml.). The catalyst (1.11 g. of 5% Pd/C) was added and the reduction was started. The hydrogen uptake was quantitative in 3¾ hours but most of the reduction was done in 1⅛ hours.

(b) Iodination

The catalyst was removed by filtration and concentrated hydrochloric acid (37.1 ml., 0.431 mol) was added to the filtrate. This solution was placed in a 2-liter, three-necked, round-bottomed flask, diluted to 670 ml. and warmed to 42° C. with an oil bath. A total of 262 ml. of $NaICl_2$ (0.618 mol) was added with stirring in three portions. Each portion was added in 8–15 minutes at 42–44.4° C. with stirring intervals of 22–23 minutes between the additions. Stirring and heating at 44° C. was continued for 3 hours followed by 15 hours stirring at 25° C. The reaction was diluted to twice its volume and the temperature was raised slowly from 25° C. to 70° C. over 2⅔ hours and heating and stirring were continued at 70–80° C. for 3½ hours. After stirring at 25° C. overnight and heating 6½ more hours at 78–84° C., the iodine uptake was 98.9%. The reaction mixture was allowed to stand for 48 hours and the product was collected to yield 117.8 g. (95.2%). Thin-layer chromatography (benzene-methyl ethyl ketone-formic acid, 90:37.5:30) revealed one major spot plus a minor trailing spot.

(c) Purification

Crude 3-amino-2,4,6-triiodo-5-trishydroxymethylacetamido-benzoic acid (117.7 g.) was dissolved in methanol (588 ml.) with 20 ml. of ammonium hydroxide and stirred overnight. A crystalline solid precipitated which stopped the magnetic stirrer. Stirring was continued for 5 hours at 25° C. and 1 hour at 0.5° C. The ammonium salt was collected and dried 1 hour at 70–90° C. to yield 103.1 g. The salt was dissolved in water (390 ml.), treated with charcoal (5.5 g.) and acidified with concentrated hydrochloric acid (28 ml.). A gum precipitated which slowly crystallized. After cooling at 5–10° C. overnight the product was collected, ground with a mortar and pestle and reslurried in water (175 ml.) at 80° C. for 1 hour. Collection and drying at 85–90° C. provided 917.5 g. of product (78% overall from the nitro compound). Thin-layer chromatography (formic acid system) revealed a single spot with a trailing trace impurity. The N.E. was found/theory 667/662.

7. Preparation of 3-Acetamido-2,4,6-Triiodo-5-trishydroxymethylacetamido-benzoic Acid; VII

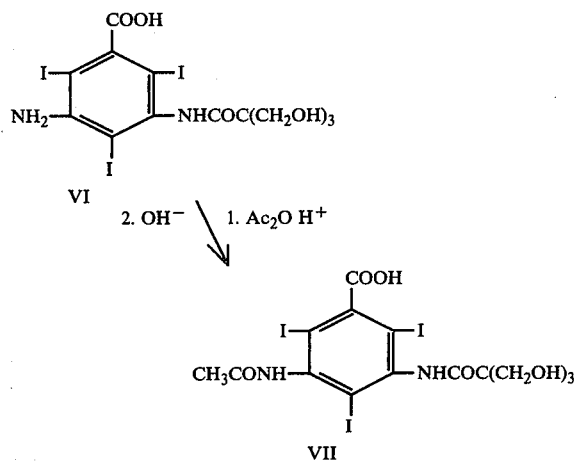

(a) Acetylation

Acetic anhydride (257 ml.) was placed in a 3-necked, 1-liter flask, 3-amino-2,4,6-triiodo-5-trishydroxymethylacetamido-benzoic acid (VI; 95.4 g., 0.14 mol) was added and the slurry was warmed to 35° C. $H_2SO_4$-acetic anhydride catalyst was added (5 ml.) and the temperature rose from 35° C. to 42.5° C. in 8–10 minutes. After stirring 7 minutes the temperature dropped to 40.5° C. and 9 ml. more catalyst was added. The catalyst was 3.5 ml. of concentrated sulfuric acid in 100 ml. of acetic anhydride which was allowed to stand for 20–25 minutes before use. The temperature dropped to 32° C. after stirring 20 minutes (total time 35–37 minutes) and heating at 50–60° C. was applied with one oil bath for 3½ hours. The solids nearly completely dissolved after 36 minutes of heating but the acetate began to crystallize. The slurry was stirred at 25° C. overnight and in an ice bath for 6 hours. The solids were collected, washed with toluene (50 ml.), reslurried in toluene (150 ml.) and washed on the Buchner funnel with toluene (100 ml.) to yield 102.91 g. (86.75%). The thin-layer chromatography (formic acid system) of the material had one minor and one major spot. The 102.91 g. was recrystallized from methanol (1.8 l.) and two crops were obtained, 68.7 g. and 18.5 g., respectively. A minor spot had been largely removed by recrystallization (thin-layer chromatography) but a trace impurity which ran below the major spot had increased in size. The yield counting both crops was 73.5% based on the amine compound (VI). The minor impurities are believed to be partly deacetylated material.

(b) Hydrolysis of the Acetate

A slurry of the acetate (67.4 g. of the first crop from the recrystallization from methanol) in water (367 ml.) was treated with 17.6 ml. of 50% sodium hydroxide (4 equivalents, 0.325 moles). The pH of the solution was monitored and the hydrolysis was followed by thin-layer chromatography at ½, 1½ and 3 hours. The pH dropped from 13.32 to 9.0 in 3 hours and 4 spots were visible in the thin-layer chromatogram. Ammonium hydroxide (60 ml.) was added in two portions and the solution was heated 2½ hours at 65–75° C. This finally gave a single spot in the thin-layer chromatogram. The solution was evaporated on the rotovapor until a pH of 7.5 was obtained (to remove excess ammonia). The solution was diluted to 1650 ml. (about 0.2 N in NaOAc and $NH_4OAc$) and passed through 600 ml. of an ion-exchange resin marketed under the trade designation "IR-120" (1.75 meq/ml. = 1050 meq) at 50–55 ml./min. The eluent was passed through a second time at 90/ml./min. and the column was washed with distilled water (2900 ml.). The eluent (3650 ml.) was taken to dryness on a rotovapor at 50° C./<0.1 mm. A pale yellow foam was obtained, yield 58.22 g., theoretical yield 57.2 g. The N.E. was found/theory 623/704. Apparently acetic acid was present. Thin-layer chromatography showed a single spot but some ammonium ion was still present as shown by a Nessler's test. The foam, 58.2 g., was recrystallized from 582 ml. of isopropyl alcohol (10 ml./g.), stored at 25° C. overnight, cooled 1½ hours at 0° C., filtered and reslurried in isopropyl alcohol (50 ml.), collected and dried at 25° C. overnight and at 75–80° C. for 2 hours to yield 53.44 g. This material traps isopropyl alcohol in the crystals so that the alcohol cannot be removed on a vacuum pump. The crystals must be dissolved in water to free the isopropyl alcohol after which all the solvents can be removed under vacuum on a rotovapor. A solution of 53.4 g. of product in 534 ml. of water (10 ml./g.) was treated with charcoal (1 g.) and concentrated to dryness on the rotovapor at 50° C. at about 1 mm. to yield 48.7 g. (85%). N.E. found/theory 707.0/704.0. Thin-layer chromatography indicated only one spot in the benzene-methyl ethyl ketone-formic acid system (90:37.5:30) and one spot with a small amount of impurity that runs above the product in the isopropyl alcohol-ammonium hydroxide system (150:40). The nuclear magnetic resonance and infrared spectra confirmed the structure.

Anal. Calcd. for $C_{14}H_{15}I_3N_2O_7$:C, 23.88%, H, 2.15%, I, 54.08%; N, 3.98%; Found: C, 24.04%; H, 2.22%; I, 53.83%; N, 4.00%

The water solubility of the product was found to be 2–2.5% w/v at 25° C.

EXAMPLE 4

The sodium salt of 3-acetamido-2,4,6-triiodo-5-trishydroxymethylacetamido-benzoic acid was prepared by conventional means. Its water solubility was found to be 63.5–66% w/v at 25° C.

Toxicity evaluations were carried out on solutions of the N-methylglucamine salt of 5-gluconamido-2,4,6-triiodo-N-methylisophthalamic acid by three different techniques and on solutions of the N-methylglucamine salt of 3-acetamido-2,4,6-triiodo-5-trishydroxymethylacetamido-benzoic acid by two different techniques. The techniques utilized are outlined below.

I. Acute Intravenous Toxicity Studies in Mice

Swiss Albino mice (Charles River) were dosed in the lateral tail vein with solutions of the iodinated compound containing 28.27% of iodine, injected at the rate of 1 ml./min. Following injections the animals were observed for immediate reactions and then daily throughout a seven day observation period. The $LD_{50}$ values were calculated by the method of Litchfield and Wilcoxon (J. of Pharmac. and Exptl. Therap. 96:99–113, 1949).

II. Intracerebral Toxicity in Mice

Swiss Albino mice (Charles River) were used. Fixed volumes of solutions of various concentrations of the iodinated compounds were injected intracerebrally via a 27 gauge needle, (¼ inch length) according to the method of Haley, et al. (Br. J. of Pharmac. 12:12–15, 1957). The animals were observed immediately after injections and daily throughout a seven day observation period. The $LD_{50}$ values were calculated by the method of Litchfield and Wilcoxon (J. of Pharmac. and Exptl. Therap. 96:99–113, 1949).

III. Intracisternal Toxicity in Rats

Sprague Dawley (Carworth) rats were used. The method used is a variation of the procedure outlined by Melartin et al. (Invest. Rad. 5:13–21, 1970). After dosing, the animals were housed individually, and observed for immediate reactions and periodically for a two day observation period. The $LD_{50}$ values were calculated according to the method of Litchfield and Wilcoxon, (J. of Pharmac. and Exptl. Therap. 96:99–115, 1949).

The results of these toxicity evaluations are set forth in Table 1.

Table 1

Toxicity Values for N-Methylglucamine Salts of 5-Gluconamido-2,4,6-Triiodo-N-Methylisophthalamic Acid and 3-Acetamido-2,4,6-Triiodo-5-Trishydroxy methylacetamido-benzoic Acid

| Acid | $LD_{50}$ of N-Methylglucamine Salt* | | |
|---|---|---|---|
| | I.V.(Mice) | Intra-cerebral (Mice) | Intra-cisternal (Rats) |
| 5-Gluconamido-2,4,6-Triiodo-N-Methyliso-phthalamic Acid | 5200 | 620 | 355 |
| 3-Acetamido-2,4,6-Triiodo-5-Trishydroxy-methylacetamido-benzoic Acid | 6000 | 150 | — |

*All $LD_{50}$ values are expressed in terms of mg. contained iodine/kg. animal body weight.

The $LD_{50}$ values for the N-methylglucamine salts of 5-gluconamido-2,4,6-triiodo-N-methylisophthalamic acid and 3-acetamido-2,4,6-triiodo-5-trishydroxymethylacetamido-benzoic acid suggest that these and other nontoxic water soluble salts of these acids would be useful x-ray contrast agents for intravenous urography and other intravascular roentgenographic procedures.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A compound of the formula:

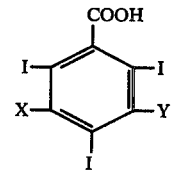

wherein X is selected from the group consisting of lower acylamino, N-(lower alkyl)-lower acylamino, N-(hydroxy lower alkyl)-lower acylamino, carbamyl and N-(lower alkyl) carbamyl and Y is gluconamido, and salts thereof with pharmaceutically acceptable cations, and esters thereof with lower alkanols.

2. A compound as defined by claim 1 which is 5-gluconamido-2,4,6-triiodo-N-methylisophthalamic acid.

3. A compound as defined by claim 1 which is a salt of 5-gluconamido-2,4,6-triiodo-N-methylisophthalamic acid with a pharmaceutically acceptable cation.

4. A compound as defined by claim 3 wherein the pharmaceutically acceptable cation is sodium.

5. A compound as defined by claim 3 wherein the pharmaceutically acceptable cation is N-methylglucamine.

6. An x-ray contrast medium comprising an aqueous solution of an effective amount of a salt of a compound of the formula:

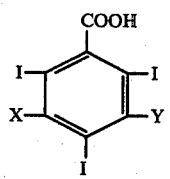

wherein X is selected from the group consisting of lower acylamino, N-(lower alkyl)-lower acylamino, N-(hydroxy lower alkyl)-lower acylamino, carbamyl and N-(lower alkyl) carbamyl and Y is gluconamido, with at least one pharmaceutically acceptable cation.

7. An x-ray contrast medium as defined by claim 6 wherein said compound is 5-gluconamido-2,4,6-triiodo-N-methylisophthalamic acid.

* * * * *